United States Patent
Sitzmann et al.

(10) Patent No.: US 9,394,244 B2
(45) Date of Patent: Jul. 19, 2016

(54) ETHYLENICALLY UNSATURATED OLIGOMERS

(71) Applicant: BASF SE, Ludwigshafen (DE)

(72) Inventors: Eugene Valentine Sitzmann, Wyandotte, MI (US); David Trumbo, Wyandotte, MI (US); Mervin Wood, Riverview, MI (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/430,934

(22) PCT Filed: Oct. 22, 2013

(86) PCT No.: PCT/US2013/066130
§ 371 (c)(1),
(2) Date: Mar. 25, 2015

(87) PCT Pub. No.: WO2014/066358
PCT Pub. Date: May 1, 2014

(65) Prior Publication Data
US 2015/0259280 A1    Sep. 17, 2015

Related U.S. Application Data

(60) Provisional application No. 61/717,327, filed on Oct. 23, 2012.

(51) Int. Cl.
| | |
|---|---|
| *C08F 2/50* | (2006.01) |
| *C08F 2/46* | (2006.01) |
| *C08G 61/04* | (2006.01) |
| *C07C 275/60* | (2006.01) |
| *C07D 401/14* | (2006.01) |
| *C07C 273/18* | (2006.01) |
| *C07D 211/94* | (2006.01) |
| *C07D 251/24* | (2006.01) |
| *C08F 222/22* | (2006.01) |
| *C09D 135/02* | (2006.01) |
| *C07D 249/20* | (2006.01) |
| *C07D 307/62* | (2006.01) |

(52) U.S. Cl.
CPC ......... *C07C 275/60* (2013.01); *C07C 273/1854* (2013.01); *C07D 211/94* (2013.01); *C07D 249/20* (2013.01); *C07D 251/24* (2013.01); *C07D 307/62* (2013.01); *C07D 401/14* (2013.01); *C08F 222/22* (2013.01); *C09D 135/02* (2013.01)

(58) Field of Classification Search
CPC ........... C07C 273/1854; C07D 211/94; C07D 251/74; C07D 401/14; C09D 135/02; C08F 222/22
USPC .................. 522/64, 6, 71, 189, 184, 1; 520/1
See application file for complete search history.

(56) References Cited

U.S. PATENT DOCUMENTS

| | | | |
|---|---|---|---|
| 4,880,859 A | * | 11/1989 | Slongo ................ C08F 293/005 524/102 |
| 5,739,251 A | | 4/1998 | Venham et al. |
| 6,617,413 B1 | | 9/2003 | Bruchmann et al. |
| 7,776,969 B2 | | 8/2010 | Adkins |
| 2002/0013462 A1 | | 1/2002 | Gupta et al. |
| 2007/0112161 A1 | | 5/2007 | Roesler et al. |
| 2009/0199351 A1 | | 8/2009 | Wood et al. |
| 2009/0269568 A1 | | 10/2009 | Kuhlmann et al. |
| 2013/0323426 A1 | | 12/2013 | Kaczun et al. |

FOREIGN PATENT DOCUMENTS

| | | | |
|---|---|---|---|
| JP | 2012-036253 | * | 2/2012 |
| KR | 10-2008-0051088 A | | 6/2008 |
| KR | 10-2008-0075119 A | | 8/2008 |
| KR | 10-2009-0113783 A | | 2/2009 |

OTHER PUBLICATIONS

Yuasa et al, JP 2012-036253 Machine Translation, Feb. 23, 2012.*
International Search Report/written opinion dated Mar. 7, 2014.

* cited by examiner

*Primary Examiner* — Ling Choi
*Assistant Examiner* — Jessica E Whiteley
(74) *Attorney, Agent, or Firm* — Foley & Lardner LLP

(57) ABSTRACT

Disclosed are functional polyallophanate oligomers comprising ethylenically unsaturated groups and polymer stabilizer groups selected from hindered amine light stabilizers, ultraviolet light absorbers, antioxidants and dihydrocarbylhydroxylamines. The ethylenically unsaturated groups and the polymer stabilizer groups are bound to the polyallophanate oligomers through allophanate and/or carbamate groups. The polyallophanate oligomers are useful in curable coatings, inks and varnishes. The present polyallophanate oligomers are derived from a) organic polyisocyanates, b) compounds containing at least one isocyanate reactive group and at least one ethylenically unsaturated group and c) polymer stabilizers containing at least one isocyanate reactive group.

9 Claims, No Drawings

ETHYLENICALLY UNSATURATED OLIGOMERS

The present invention relates to oligomers containing ethylenically unsaturated groups and further containing polymer stabilizer groups. The polymer stabilizers are for example selected from the group consisting of hindered amine light stabilizers (HALS), ultraviolet light absorbers (UVAs), antioxidants and dihyrocarbylhydroxylamines.

It has been found that certain polymer stabilizers, when covalently bound to certain curable oligomers, perform exceptionally well in curable compositions. The bound stabilizers are highly compatible. The ethylenically unsaturated groups and the polymer stabilizers are bound to the oligomer through allophanate and/or carbamate groups.

Accordingly, the present invention is aimed at oligomer compounds containing ethylenically unsaturated groups bound through allophanate groups and/or carbamate groups and containing one or more polymer stabilizer groups bound through allophanate groups and/or carbamate groups.

The present oligomer compounds are derived from a) organic polyisocyanates, b) compounds containing at least one isocyanate reactive group and at least one ethylenically unsaturated group and c) compounds containing at least one isocyanate reactive group and at least one polymer stabilizer group.

The process for preparing the present oligomer compounds comprises reacting a) at least one organic polyisocyanate with b) at least one compound containing at least one isocyanate reactive group and at least one ethylenically unsaturated group to prepare an intermediate with allophanate bound ethylenically unsaturated groups and unreacted isocyanate groups, followed by reacting the intermediate with c) at least one compound containing at least one isocyanate reactive group and at least one polymer stabilizer group.

The order in the above 2 step process may also be reversed. In this case a) would be reacted first with c) to prepare an intermediate, followed by reacting the intermediate with b). In this case the intermediate would contain allophanate bound polymer stabilizer groups and unreacted isocyanate groups.

Alternatively, the present process comprises reacting a) at least one polyisocyanate, b) at least one compound comprising at least one isocyanate reactive group and at least one ethylenically unsaturated group and c) at least one compound containing at least one isocyanate reactive group and at least one polymer stabilizer group in a 1 step process without the preparation of any intermediate.

In the 2 step processes, an intermediate containing allophanate groups is formed. This intermediate may be isolated. The intermediate containing allophanate groups contains at least 1 unreacted isocyanate group. The intermediate advantageously contains 2, 3 or 4 isocyanate groups, normally 2.

The number average molecular weight, Mn, of the present oligomers is less than 10,000 g/mol, preferably less than 5000 g/mol, more preferably less than 4000 g/mol and most preferably is 2000 g/mol or less. Preferably the number average molecular weight is from about 900 to about 3000 g/mol, more preferably from about 1000 to about 2500 g/mol and most preferably from about 1000 to about 2000 g/mol.

The term "derived from" means that oligomer contains these groups as monomer units or end groups.

The amount of allophanate groups, $C_2N_2HO_3$, in the oligomers is generally from about 3% to about 25% by weight.

The present general process may follow those taught in U.S. Pat. Nos. 5,739,251 and 6,617,413 and U.S. application Ser. No. 13/905,514, the contents of which are hereby incorporated by reference. The processes of this invention may employ necessary catalysts and temperature ranges as described therein.

The present process may be performed neat, or may be performed with a suitable solvent. Suitable solvents include acetone, isobutyl methyl ketone, toluene, xylene, butyl acetate, methoxypropyl acetate, ethoxyethyl acetate and ethyl acetate.

A suitable catalyst may be employed, for instance metal compounds, amine compounds or ammonium compounds, for example zinc acetylacetonate, zinc 2-ethylcaproate, di-n-butyltindilaurate, zinc octoate, tin(II) octoate, triethylamine, dimethyl ethanolamine, N,N,N-trimethyl-N-2-hydroxypropylammonium hydroxide or N, N, N-trimethyl-N-2-hydroxypropylammonium 2-ethyl hexanoate.

Temperatures of from about 30° C. to about 200° C. or to about 160° C. are generally employed for allophanate and carbamate formation.

The oligomers of this invention may be visualized as one of the following structures:

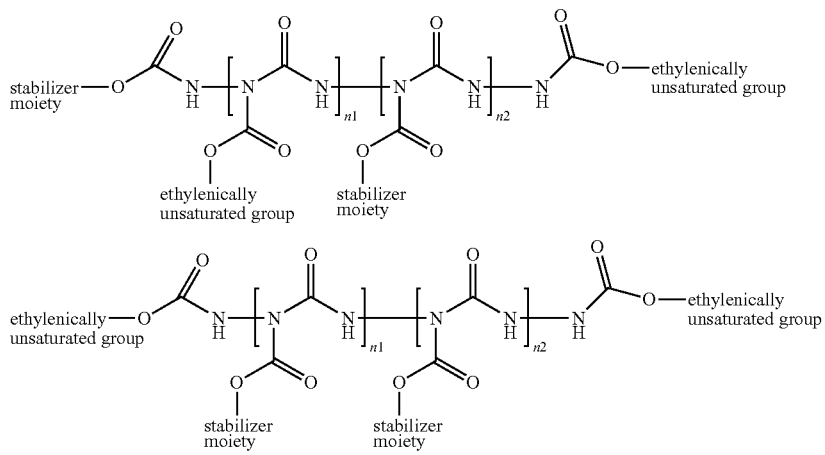

-continued

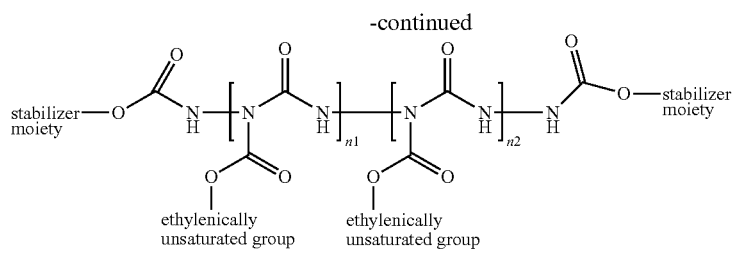

The number of allophanate groups is generally 1, 2, 3, 4 or 5.

The end groups may also be unreacted isocyanate groups. The groups n1 and n2 represent repeating units of 1 and above and may also be zero. The groups n1 and n2 are not both zero. The present oligomer compounds include at least one stabilizer moiety and at least one ethylenically unsaturated group. The groups n1 and n2 may be random or block.

It is not necessary that all isocyante groups be converted to allophanate or carbamate groups. The final polyallophanate oligomer products may contain residual isocyanate groups.

The present oligomers may contain some groups other than allophanate, carbamate and/or isocyanate groups. Such groups would normally be in minor amounts and are other possible reaction products of isocyanate groups.

For example, the present oligomers may contain residual isocyanate groups or may contain less than 0.4, 0.3, 0.2 or less than 0.1% by weight of free isocyanate groups by weight. When isocyanate groups are present, the oligomers are useful in dual cure systems, with both curable isocyanate groups and curable ethylenically unsaturated groups. Oligomers containing residual isocyanate groups contain for example 1 or 2 isocyanate groups.

The polyisocyanates are preferably diisocyanates having 4 to 20 C atoms. Examples are tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, tetramethylxylylene diisocyanate, trimethylhexane diisocyanate or tetramethylhexane diisocyanate, cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4- or 2,6-diisocyanato-1-methylcyclohexane, and also aromatic diisocyanates such as tolylene 2,4- or 2,6-diisocyanate and the isomer mixtures thereof, m- or p-xylylene diisocyanate, 2,4'- or 4,4'-diisocyanato-diphenylmethane and the isomer mixtures thereof, phenylene 1,3- or 1,4-diisocyanate, 1-chlorophenylene 2,4-diisocyanate, naphthylene 1,5-diisocyanate, diphenylene 4,4'-diisocyanate, 4,4'-diisocyanato-3,3'-dimethylbiphenyl, 3-methyldiphenylmethane 4,4'-diisocyanate, tetramethylxylylene diisocyanate, 1,4-diisocyanatobenzene or diphenyl ether 4,4'-diisocyanate.

The organic polyisocyanate is preferably selected from aliphatic, cycloaliphatic and aromatic diisocyanates, such as 1,4-diisocyanatobutane, 1,5-diisocyanatopentane, hexamethylene diisocyanate (HDI), 1,11-diisocyanatoundecane, 1,12-diisocyanatododecane, 2,2,4- and 2,4,4-trimethyl-1,6-diisocyanatohexane, 1-isocyanato-3,3,5-trimethyl-5-isocyanatomethyl cyclohexane (IPDI, isophorone diisocyanate), 1,3-diisocyanatocyclobutane, 1,3- and 1,4-diisocyanatocyclohexane, 4,4'-bis-(isocyanatocyclohexyl)-methane (HMDI), 1,2-bis-(isocyanatomethyl)-cyclobutane, 1,3- and 1,4-bis-(isocyanatomethyl)-cyclohexane, hexahydro-2,4- and/or -2,6-diisocyanatotoluene, bis-isocyanatomethyl norbornane (isomer mixture), 2,5- and 2,6-bis-(isocyanatomethyl)-bicyclo[2.2.1]heptane, 1-isocyanato-4(3)-isocyanatomethyl-1-methyl cyclohexane, p-xylylene diisocyanate, 2,3-bis-(8-isocyanatooctyl)-4-octyl-5-hexyl cyclohexane and mixtures thereof.

Preferably, the polyisocyanate is IPDI, HMDI or HDI and most preferably is HDI. Also preferred is 1,3-bis(isocyanatomethyl)cyclohexane.

The isocyanate reactive groups are for instance —OH, —SH, —NH$_2$ or —NHR, where R is an alkyl group of from 1 to 4 carbon atoms, for instance methyl, ethyl, n-propyl, isopropyl, n-butyl, isobutyl, sec-butyl or tert-butyl.

Compounds b) and c) containing isocyanate reactive groups —OH, —SH, —NH$_2$ or —NHR are referred to as hydroxy, thio or amino functional compounds. Compounds b) and c) preferably contain from 1 to 3 isocyanate reactive groups.

The compounds b) preferably have one isocyanate reactive group and 1 to 3 ethylenically unsaturated groups.

The compounds b) may be, for example, monoesters of α,β-unsaturated carboxylic acids, such as acrylic acid, methacrylic acid, crotonic acid, itaconic acid, fumaric acid, maleic acid, acrylamidoglycolic acid or methacrylamidoglycolic acid, with alcohols which have preferably 2 to 20 C atoms and at least two hydroxyl groups, such as ethylene glycol, diethylene glycol, triethylene glycol, propylene 1,2-glycol, propylene 1,3-glycol, 1,1-dimethyl-1,2-ethanediol, dipropylene glycol, triethylene glycol, tetraethylene glycol, pentaethylene glycol, tripropylene glycol, 1,2-, 1,3- or 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, 2,2-bis(4-hydroxycyclohexyl)propane, glycerol, trimethylolethane, trimethylolpropane, trimethylolbutane, pentaerythritol, ditrimethylolpropane, erythritol, sorbitol, polyethylene glycol having a molar mass of between 106 and 2000, polypropylene glycol having a molar weight of between 134 and 2000, polytetrahydrofuran having a molar weight of between 162 and 2000 or poly-1,3-propanediol having a molar weight of between 134 and 400. In addition it is also possible to use esters or amides of (meth)acrylic acid with amino alcohols such as 2-aminoethanol, 2-(methylamino)ethanol, 3-amino-1-propanol, 1-amino-2-propanol or 2-(2-aminoethoxyl)ethanol, for example, 2-mercaptoethanol or polyaminoalkanes, such as ethylenediamine or diethylenetriamine, or vinylacetic acid.

Also suitable are unsaturated polyetherols or polyesterols or polyacrylate polyols having an average OH functionality of 2 to 10.

Examples of amides of ethylenically unsaturated carboxylic acids with amino alcohols are hydroxyalkyl(meth)acrylamides such as N-hydroxymethylacrylamide, N-hydroxymethylmethacrylamide, N-hydroxyethylacrylamide, N-hydroxyethyl methacrylamide, 5-hydroxy-3-oxapentyl (meth)acrylamide, N-hydroxyalkylcrotonamides such as N-hydroxymethylcrotonamide or N-hydroxyalkylmaleimides such as N-hydroxyethylmaleimide.

Preference is given to 2-hydroxyethyl(meth)acrylate, 2- or 3-hydroxypropyl(meth)acrylate, 1,4-butanediol mono(meth)acrylate, neopentyl glycol mono(meth)acrylate, 1,5-pentanediol mono(meth)acrylate, 1,6-hexanediol mono(meth)acrylate, glycerol mono(meth)acrylate and di(meth)acrylate, trimethylolpropane mono(meth)acrylate and di(meth)acrylate, pentaerythritol mono(meth)acrylate, di(meth)acrylate, and tri(meth)acrylate, and also 2-aminoethyl(meth)acrylate, 2-aminopropyl(meth)acrylate, 3-aminopropyl(meth)acrylate, 4-aminobutyl(meth)acrylate, 6-aminohexyl(meth)acrylate, 2-thioethyl(meth)acrylate, 2-aminoethyl(meth)acrylamide, 2-aminopropyl(meth)acrylamide, 3-aminopropyl(meth)acrylamide, 2-hydroxyethyl(meth)acrylamide, 2-hydroxypropyl(meth)acrylamide, or 3-hydroxypropyl(meth)acrylamide. Particularly preferred are 2-hydroxyethyl acrylate, 2-hydroxyethyl methacrylate, 2- or 3-hydroxypropyl acrylate, 1,4-butanediol monoacrylate, 3-(acryloyloxy)-2-hydroxypropyl(meth)acrylate and also the monoacrylates of polyethylene glycol with a molar mass of 106 to 238.

In one preferred embodiment, component b) may also comprise technical mixtures from the acrylation of trimethylolpropane, pentaerythritol, ditrimethylolpropane or dipentaerythritol, or alkoxylated, preferably propoxylated and/or ethoxylated, more preferably ethoxylated, trimethylolpropane, pentaerythritol, ditrimethylolpropane or dipentaerythritol. These are mostly mixtures of completely and incompletely acrylated polyols; for example, compounds b) are technical mixtures from the acrylation of pentaerythritol that usually have an OH number to DIN 53240 of 99 to 115 mg KOH/g and consist predominantly of pentaerythritol triacrylate and pentaerythritol tetraacrylate, and may also contain minor amounts of pentaerythritol diacrylate. This has the advantage that pentaerythritol tetraacrylate is not incorporated into the oligomers of the invention, but instead functions simultaneously as a reactive diluent.

Preferably, the compounds b) are selected from the group consisting of allyl alcohol, 2-hydroxyethyl vinyl ether, 4-hydroxybutyl vinyl ether, glycerol diallyl ether, trimethylolpropane diallyl ether, pentaerythritol triallyl ether, 2-hydroxyethylacrylate, 2-hydroxyethylmethacylate, polyethylene glycol acrylate, polyethylene glycol methacrylate, glycerol diacrylate, glycerol dimethacrylate, trimethyolpropane diacrylate, trimethyolpropane dimethacrylate, pentaerythritol triacrylate and pentaerythritol trimethacrylate.

The compounds c) are selected from the group consisting of hindered amine light stabilizers (HALS), ultraviolet light absorbers (UVAs), antioxidants and dihydrocarbylhydroxylamines that contain isocyanate reactive groups.

The compounds c) generally have one isocyanate reactive group and one polymer stabilizer group.

The HALS are taught for instance in U.S. Pat. Nos. 5,004,770, 5,204,473, 5,096,950, 5,300,544, 5,112,890, 5,124,378, 5,145,893, 5,216,156, 5,844,026, 5,980,783, 6,046,304, 6,117,995, 6,271,377, 6,297,299, 6,392,041, 6,376,584 and 6,472,456. The contents of these U.S. Patents are incorporated by reference.

The hindered amine light stabilizers for example include 1 to 3 isocyanate reactive groups and include at least one moiety

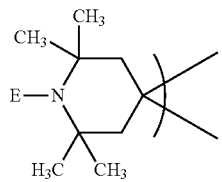

where E is O$^+$, hydrogen, straight or branched C$_1$-C$_8$alkyl, C$_5$-C$_{10}$cycloalkyl, straight or branched C$_1$-C$_8$alkoxy, C$_5$-C$_{10}$cycloalkoxy, 2-hydroxy-2-methylpropoxy, 2-hydroxycyclohexyloxy, 2-hydroxy-1-phenethoxy or acetoxy.

Preferably, E is O$^+$, hydrogen, methyl, octyloxy, cyclohexyloxy, 2-hydroxy-2-methylpropoxy or acetoxy.

For instance, suitable hindered amines are H1-H11:

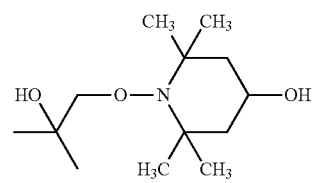

H1

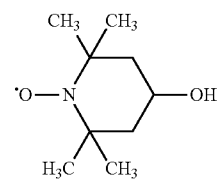

H2

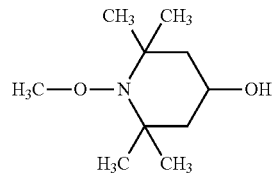

H3

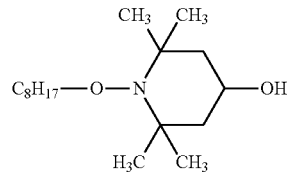

H4

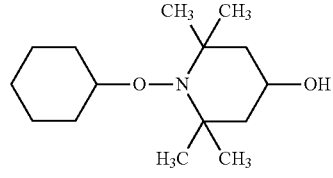

H5

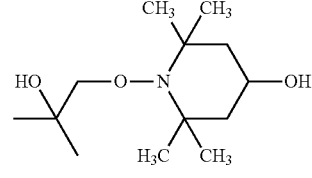

H6

-continued

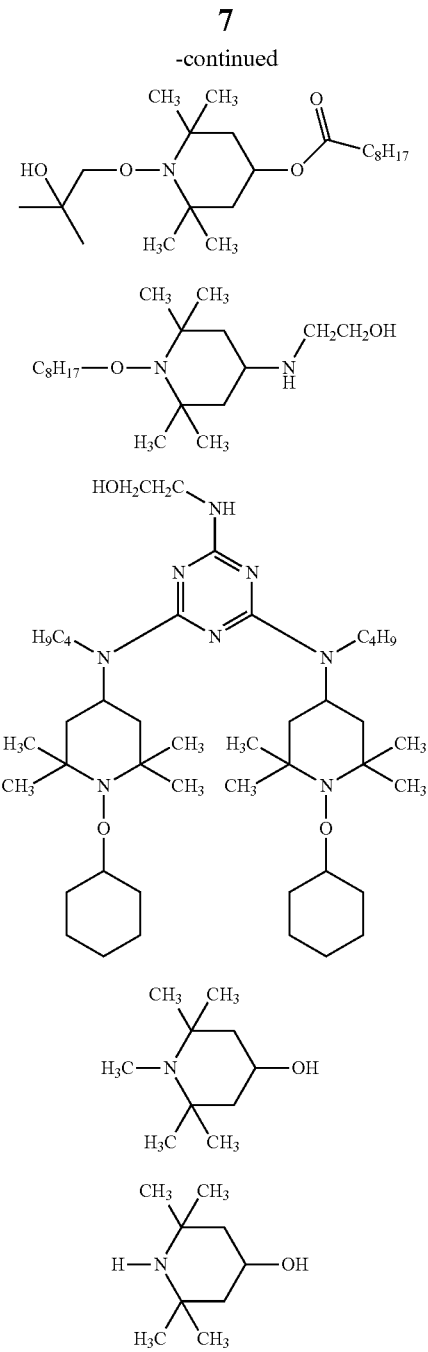

H7

H8

H9

H10

H11

The UVAs are for instance hydroxyphenylbenzotriazoles, taught in U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987; 5,977,219 and 6,166,218, each incorporated herein by reference.

The UVAs are also for example tris-aryl-s-triazines, taught in U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,736,597; 5,942,626; 5,959,008; 5,998,116; 6,013,704; 6,060,543; 6,242,598 and 6,255,483, each hereby incorporated by reference.

The UVAs are also for instance hydroxybenzophenones, for instance 2,4-dihydroxybenzophenone or 4,2',4'-trihydroxybenzophenone.

The ultraviolet light absorbers for instance include 1 to 3 isocyanate reactive groups and include at least one moiety

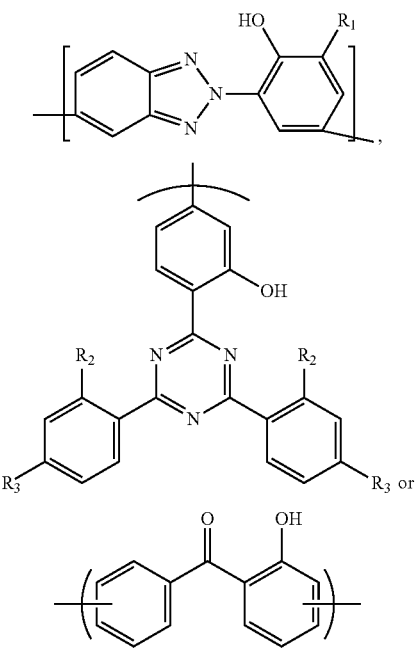

where $R_1$ is hydrogen, tert-butyl or alpha-cumyl, $R_2$ is hydrogen or methyl and $R_3$ is hydrogen, methyl or phenyl.

For example, suitable UVAs are UV1-UV7:

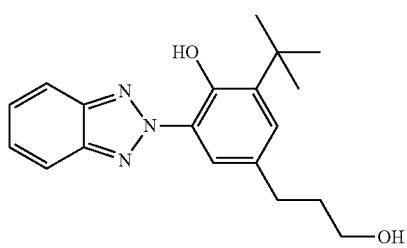

UV1

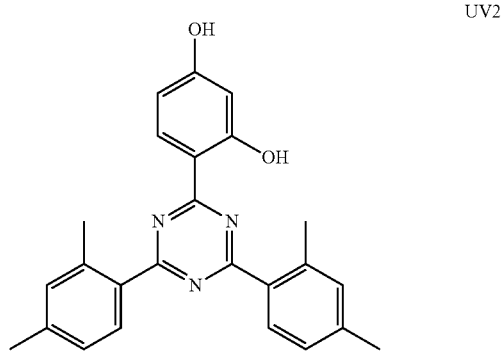

UV2

UV3
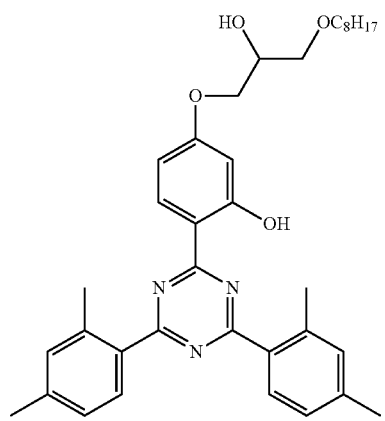

UV4
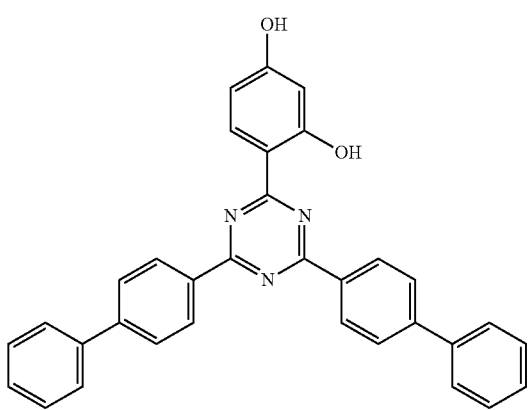

UV5
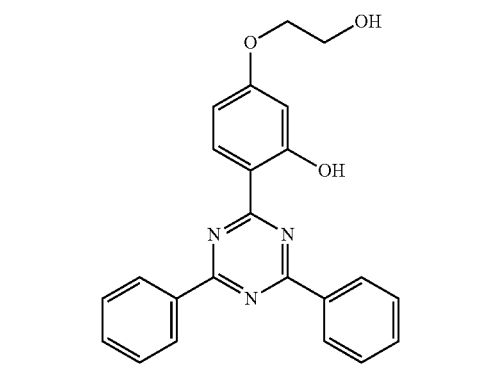

UV6
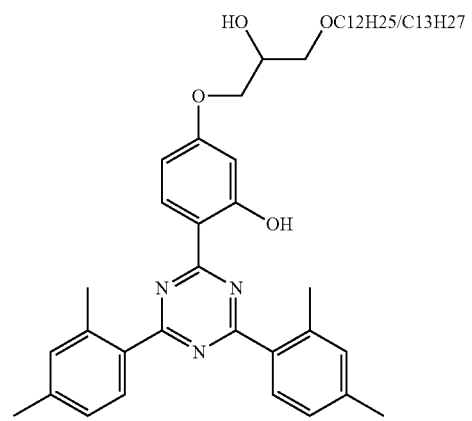

UV7
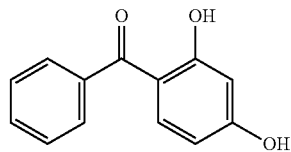

The phenolic OH that interacts with the triazole or triazine ring is not an isocyanate reactive group. In this instance, the term "containing 1 to 3 hydroxy groups" excludes this phenolic OH.

The present dihydrocarbylhydroxylamines contain for example 1 to 3 isocyanate reactive groups and include at least one moiety

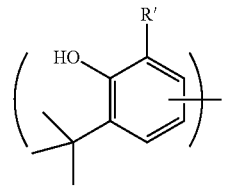

In the dihydrocarbylhydroxylamines, the hydroxyl of the hydroxylamine is isocyanate reactive.

The dihydrocarbylhydroxylamines are for example N,N-dibenzylhydroxylamine, N,N-diethylhydroxylamine, N,N-dihexylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine or N,N-di($C_{16}$-$C_{18}$alkyl) hydroxylamine.

The antioxidants are for instance hindered phenolic compounds that contain 1 to 3 isocyanate reactive groups and one or more moieties

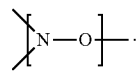

where R' is methyl or t-butyl.

For instance, suitable antioxidants are:

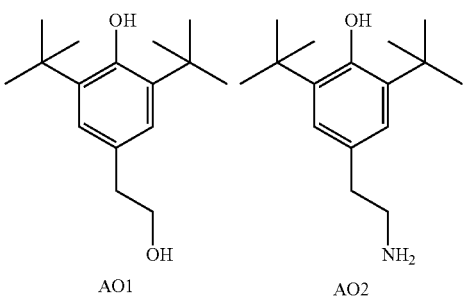

AO1  AO2

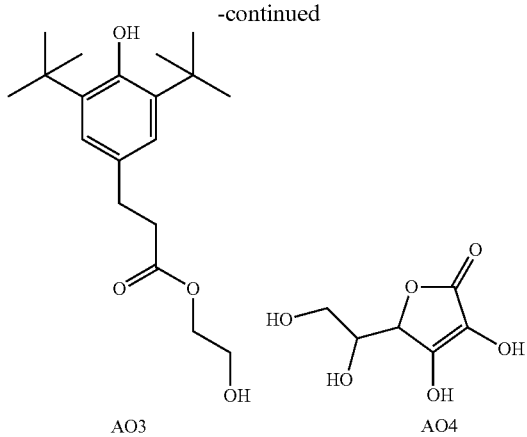

AO3  AO4

The hindered phenol hydroxy group is not isocyanate reactive.

There are generally 1, 2, 3 or 4 "moieties" (stabilizer moieties) present in the polymer stabilizer compounds.

The curable compositions according to the invention are in particular coatings, inks or varnishes.

The curable compositions containing the oligomers of the present invention may be cured with ultraviolet light, sunlight, electron beam or at elevated temperatures in the presence of peroxides or azo compounds or under ambient conditions with metal siccatives in the presence of oxygen or peroxides. Curing may take place in the presence of a suitable photoinitiator. The present oligomers are radiation curable and/or thermally curable through the ethylenically unsaturated groups. Dual cure is also possible, employing the above methods and also isocyanate curing. Isocyanate curing occurs upon contact with certain isocyanate reactive compounds, for instance water, alcohols or amines.

The compositions containing the present oligomers are useful to coat substrates of any kind, for instance wood, plastics, leather, paper, textiles, glass, ceramics, plaster, masonry, metals or concrete. They may be applied by methods including spray coating, spread coating, flood casting, casting, dip coating and roll coating. The coatings may be clear or pigmented.

Suitable substrates preferably include polyamides, polyethylene, polypropylene, polyesters such as polyethylene terephthalate, polystyrene, paper, paperboard, cardboard, plastic coated paper, plastic coated paperboard, plastic coated cardboard, aluminum and aluminum coated polymer films.

Substrates preferably include polyethylene, polypropylene, polyesters, paper and cardboard.

The present oligomers may be the sole binder in the coatings, inks and varnishes, or may contain additional curable ethylenically unsaturated compounds or binders.

Additional curable ethylenically unsaturated compounds contain radically polymerizable groups, for example, preferably (meth)acrylate groups and more preferably acrylate groups.

The additional ethylenically unsaturated compounds are preferably polyfunctional (more than one radically polymerizable double bond) polymerizable compounds.

(Meth)acrylic acid stands in this specification for methacrylic acid or acrylic acid, preferably for acrylic acid.

Multifunctional polymerizable compounds are preferably multifunctional(meth)acrylates which carry at least 2, preferably 2-10, more preferably 3-6, and very preferably 3-4 (meth)acrylate groups, preferably acrylate groups.

Examples of multifunctional polymerizable compounds are ethylene glycol diacrylate, 1,2-propanediol diacrylate, 1,3-propanediol diacrylate, 1,4-butanediol diacrylate, 1,3-butanediol diacrylate, 1,5-pentanediol diacrylate, 1,6-hexanediol diacrylate, 1,8-octanediol diacrylate, neopentyl glycol diacrylate, 1,1-, 1,2-, 1,3-, and 1,4-cyclohexanedimethanol diacrylate, 1,2-, 1,3- or 1,4-cyclohexanediol diacrylate, dipropylene glycol diacrylate, trimethylolpropane triacrylate, ditrimethylolpropane tipropylene glycol diacrylate penta- or hexaacrylate, pentaerythritol tri- or tetraacrylate, glycerol di- or triacrylate, and also di- and polyacrylates of sugar alcohols, such as sorbitol, mannitol, diglycerol, threitol, erythritol, adonitol (ribitol), arabitol (lyxitol), xylitol, dulcitol (galactitol), maltitol or isomalt, or of polyester polyols, polyetherols, poly THF having a molar mass of between 162 and 2000, poly-1,3-propanediol having a molar mass of between 134 and 1178, polyethylene glycol having a molar mass of between 106 and 898, and also epoxy tetraacrylate dipentaerythritol(meth)acrylates, polyester(meth)acrylates, polyether(meth)acrylates, urethane (meth)acrylates or polycarbonate(meth)acrylates, which optionally may also have been modified with one or more amines.

U.S. patents, U.S. published patent applications and U.S. patent applications mentioned herein are hereby incorporated by reference.

Each of the terms "a", "one or more" and "at least one" are interchangeable.

Specifically, the following embodiments are disclosed.

Embodiment 1

An oligomer containing one or more ethylenically unsaturated groups bound through allophanate groups and/or carbamate groups and containing one or more polymer stabilizer groups selected from the group consisting of hindered amine light stabilizers, ultraviolet light absorbers, antioxidants and dihydrocarbylhydroxylamines bound through allophanate groups and/or carbamate groups.

Embodiment 2

An oligomer according to embodiment 1 which is derived from a) one or more organic polyisocyanates, b) one or more compounds containing at least one isocyanate reactive group and at least one ethylenically unsaturated group and c) one or more compounds containing at least one isocyanate reactive group and at least one polymer stabilizer group.

Embodiment 3

An oligomer according to embodiment 1 which is derived from
a) one or more polyisocyanates selected from the group consisting of 1,4-diisocyanatobutane, 1,5-diisocyanatopentane, 1,6-diisocyanatohexane (HDI), 1,11-diisocyanatoundecane, 1,12-diisocyanatododecane, 2,2,4- and 2,4,4-trimethyl-1,6-diisocyanatohexane, 1-isocyanato-3,3,5-trimethyl-5-isocyanatomethyl cyclohexane (IPDI), 1,3-diisocyanatocyclobutane, 1,3- and 1,4-diisocyanatocyclohexane, 4,4'-bis-(isocyanatocyclohexyl)-methane (HMDI), 1,2-bis-(isocyanatomethyl)-cyclobutane, 1,3- and 1,4-bis-(isocyanatomethyl)-cyclohexane, hexahydro-2,4- and/or -2,6-diisocyanatotoluene, bis-isocyanatomethyl norbornane (isomer mixture), 2,5- and 2,6-bis-(isocyanatomethyl)-bicyclo[2.2.1]heptane, 1-isocyanato-4(3)-isocyanatomethyl-1-methyl cyclohexane, p-xylylene diisocyanate and 2,3-bis-(8-isocyanatooctyl)-4-octyl-5-hexyl cyclohexane, b) one or more compounds selected from the group consisting of allyl alcohol, 2-hydroxyethyl vinyl ether, 4-hydroxybutyl vinyl ether, glycerol diallyl ether, trimethylolpropane diallyl ether, pentaerythritol triallyl ether, 2-hydroxyethylacrylate, 2-hydroxyethylmethacrylate, polyethylene glycol acrylate, polyethylene glycol methacrylate, glycerol diacrylate, glycerol dimethacrylate, trimethyolpropane diacrylate, trimethylolpropane dimethacrylate, pentaerythritol triacrylate, and pentaerythritol trimethacrylate and c) one or more polymer stabilizers selected from the group consisting of hindered amine light stabilizers, ultraviolet light absorbers, antioxidants and dihydrocarbylhydroxylamines and containing at least one isocyanate reactive group.

Embodiment 4

An oligomer according to embodiment 2 derived from

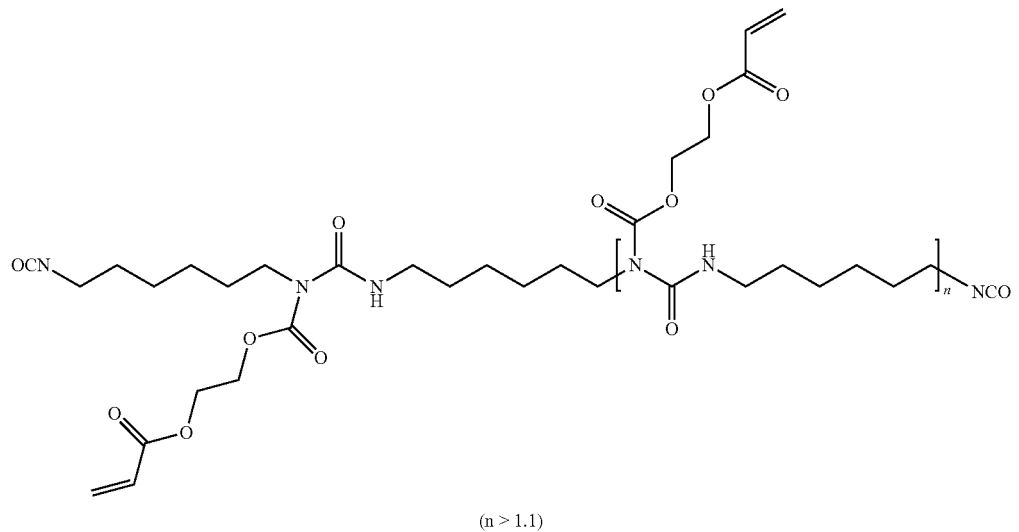

(n > 1.1)

and c) one or more compounds containing at least one isocyanate reactive group and at least one polymer stabilizer group.

Embodiment 5

An oligomer according to embodiments 2, 3 or 4 derived from c) one or more hindered amine light stabilizers comprising 1 to 3 isocyanate reactive groups and one or more moieties

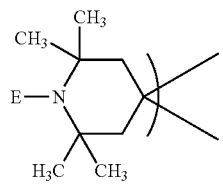

where E is $O^+$, hydrogen, straight or branched $C_1$-$C_8$alkyl, $C_5$-$C_{10}$cycloalkyl, straight or branched $C_1$-$C_8$alkoxy, $C_5$-$C_{10}$cycloalkoxy, 2-hydroxy-2-methylpropoxy, 2-hydroxycyclohexyloxy, 2-hydroxy-1-phenethoxy or acetoxy.

Embodiment 6

An oligomer according to embodiments 2, 3 or 4 derived from c) one or more ultraviolet light absorbers comprising 1 to 3 isocyanate reactive groups and one or more moieties

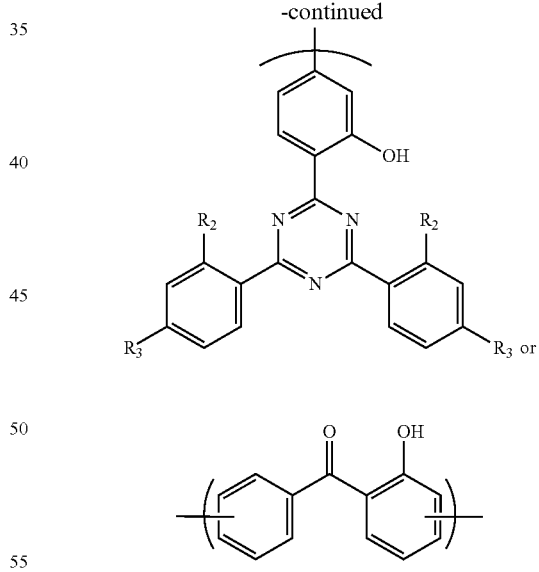

where $R_1$ is hydrogen, tert-butyl or alpha-cumyl, $R_2$ is hydrogen or methyl and $R_3$ is hydrogen, methyl or phenyl.

Embodiment 7

An oligomer according to embodiments 2, 3 or 4 derived from c) one or more antioxidants comprising 1 to 3 isocyanate reactive groups and one or more moieties where R' is methyl or t-butyl.

Embodiment 8

An oligomer according to embodiments 2, 3 or 4 derived from c) one or more dihydrocarbylhydroxylamines comprising 1 to 3 isocyanate reactive groups and one or more moieties Embodiment 9

An oligomer according to any of embodiments 2, 3 or 4 derived from c) one or more compounds selected from the group consisting of H1-H11, UV1-UV7, AO1-AO4,

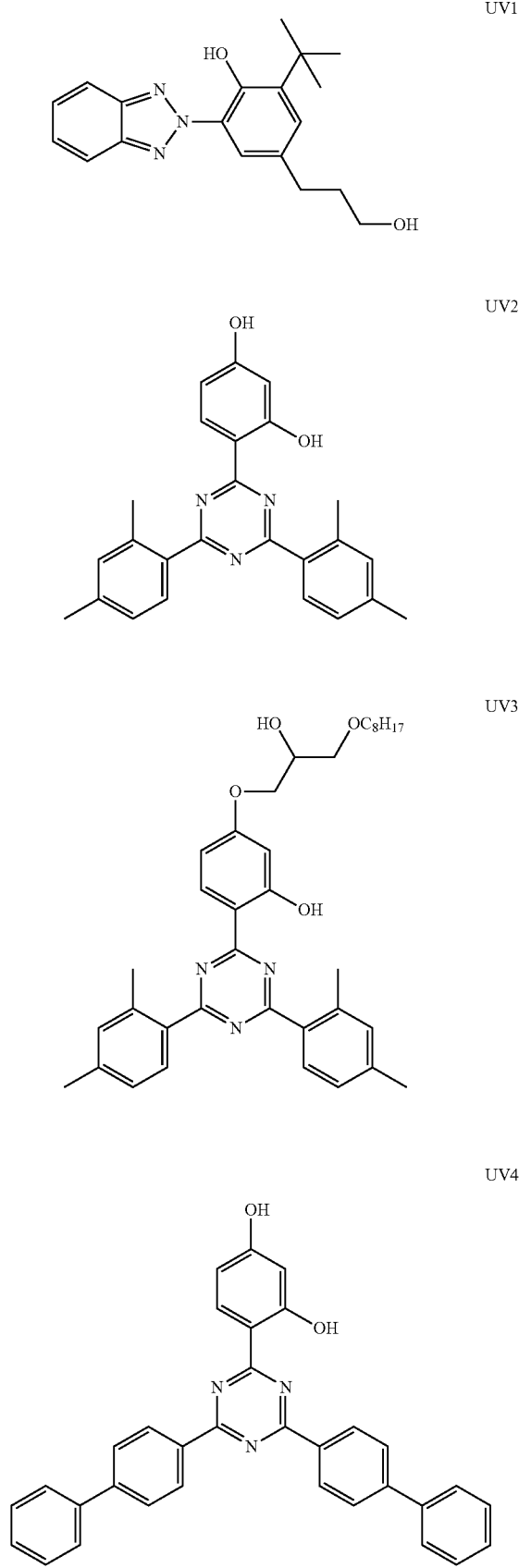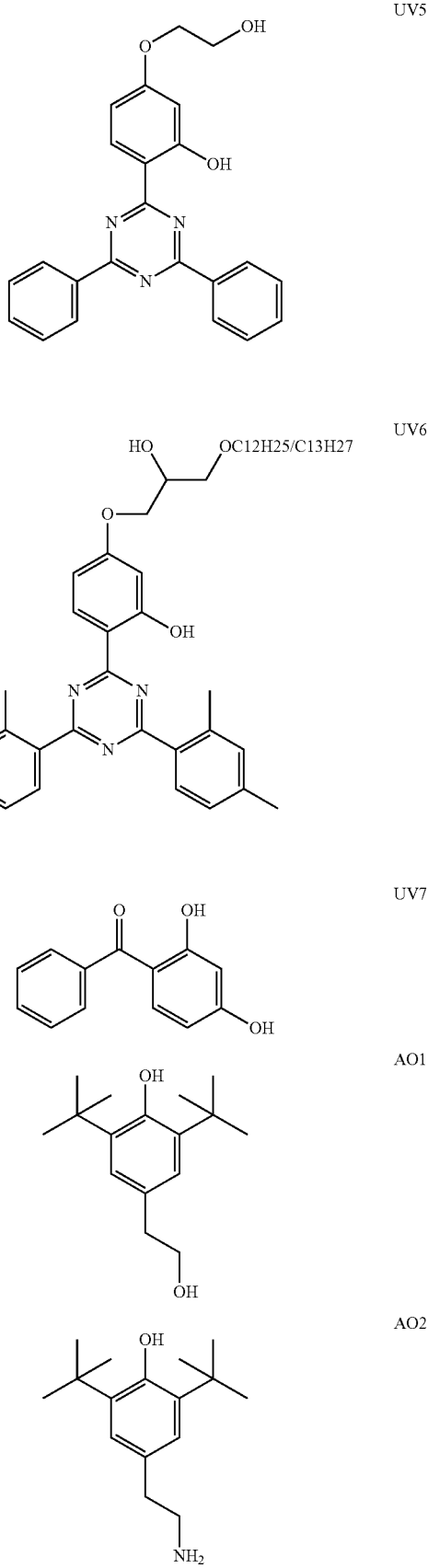

-continued

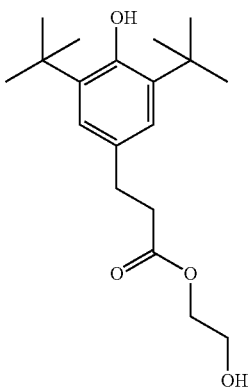
AO3

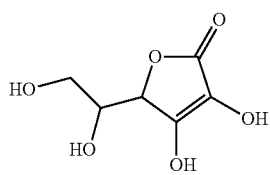
AO4

N,N-dibenzylhydroxylamine, N,N-diethylhydroxylamine, N,N-dihexylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine and N,N-di($C_{16}$-$C_{18}$alkyl)hydroxylamine.

Embodiment 10

An oligomer according to any of the preceding embodiments where the number average molecular weight is from about 900 to about 3000 g/mol, preferably from about 1000 to about 2500 g/mol and more preferably from about 1000 to about 2000 g/mol.

Embodiment 11

A curable coating, ink or varnish composition comprising an oligomer according to any of the preceding embodiments.

Embodiment 12

A curable composition according to embodiment 11 further comprising a photoinitiator.

Embodiment 13

A process for the preparation of an oligomer according to embodiments 1 to 10, which process comprises reacting a) one or more organic polyisocyanates, b) one or more compounds containing at least one isocyanate reactive group and at least one ethylenically unsaturated group and c) one or more compounds containing at least one isocyanate reactive group and at least one polymer stabilizer group selected from the group consisting of hindered amine light stabilizers, ultraviolet light absorbers, antioxidants and dihydrocarbylhydroxylamines, neat or in the presence of a suitable solvent, in the presence of a suitable catalyst and at a suitable temperature.

Embodiment 14

A process according to embodiment 13 where
a) and b) are reacted to form an intermediate with allophanate bound ethylenically unsaturated groups and unreacted isocyanate groups, followed by reacting the intermediate with c) or
a) and c) are reacted to form an intermediate with allophanate bound polymer stabilizer groups and unreacted isocyanate groups, followed by reacting the intermediate with b) or
a), b) and c) are reacted in a 1 step process.

Embodiment 15

Use of an oligomer according to any of embodiments 1 to 10 as a curable binder in a coating, ink or varnish composition.

The following Examples more particularly point out the invention. Parts and percentages are by weight unless defined otherwise.

EXAMPLE S1

Curable Oligomers Containing Polymer Stabilizer Groups

An ethylenically unsaturated allophanate intermediate is prepared according to Example 1 of U.S. Pat. No. 5,739,251, employing 1,6-hexamethylene diisocyanate and trimethyolpropane diallylether. The intermediate product is further reacted with UV5 to prepare a final oligomer of the invention.

The above example is repeated replacing UV5 with a hydroxy functional HALS selected from H1-H11, with a hydroxy functional UVA selected from UV1-UV4 and UV6, with an antioxidant selected from AO1-AO4 and with dibenzylhydroxylamine, dihexylhydroxylamine, diethylhydroxylamine and N,N-di($C_{16}$-$C_{18}$alkyl)hydroxylamine and with mixtures of the different polymer stabilizers.

The above example is repeated, employing in place of HDI, IPDI and HMDI.

The above examples are repeated, employing in place of trimethyolpropane diallyl ether a compound selected from 2-hydroxyethyl vinyl ether, 4-hydroxybutyl vinyl ether, glycerol diallyl ether, pentaerythritol triallyl ether, 2-hydroxyethylacrylate, 2-hydroxyethylmethacylate, polyethylene glycol acrylate, polyethylene glycol methacrylate, glycerol diacrylate, glycerol dimethacrylate, trimethyolpropane diacrylate, trimethyolpropane dimethacrylate, pentaerythritol triacrylate and pentaerythritol trimethacrylate.

The above examples are repeated, reacting the isocyanates first with the hydroxy functional HALS and/or UVAs, followed by reaction with the component comprising an hydroxy group and at least one ethylenically unsaturated group.

The above examples are repeated, reacting the components in a 1 step process, that is adding all reactants together in one step and reacting them to prepare the final product without preparing an intermediate allophanate with unreacted isocyanate groups.

In the following preparation Examples, the isocyanate functional intermediate allophanate employed is:

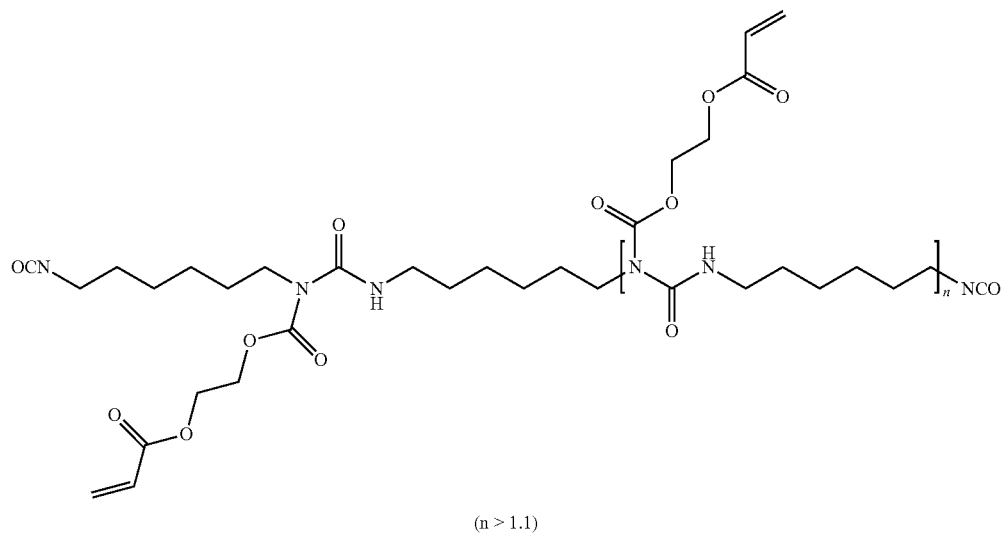

(n > 1.1)

The NCO content is from about 14.5 to about 15.5% by weight.

EXAMPLE S2

Curable Oligomer Containing Hindered Amine Light Stabilizer Groups

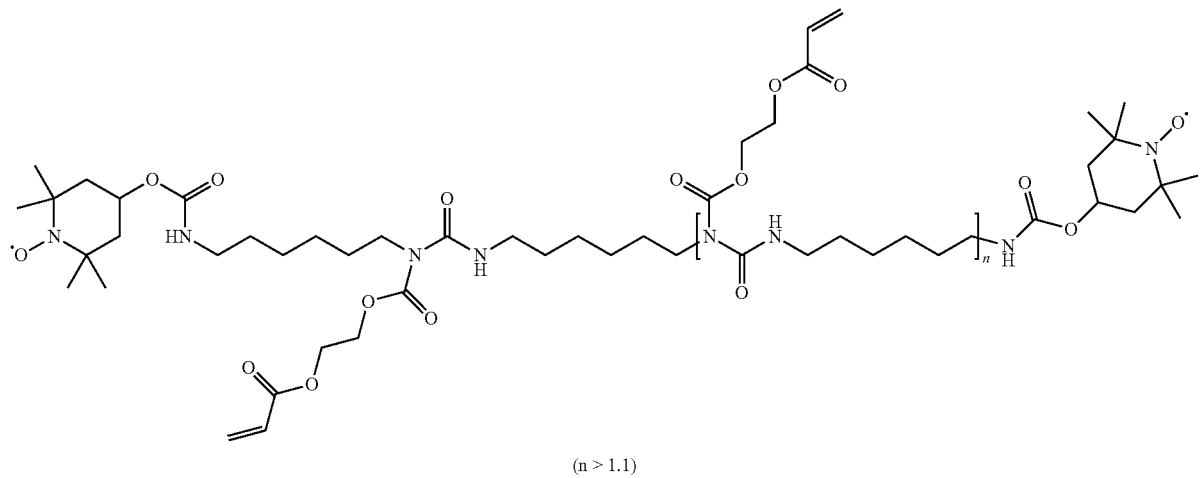

(n > 1.1)

156.1 parts (approximately 0.279 moles, approximately 0.557 moles of NCO groups) of the isocyanate functional intermediate allophanate, 94.75 parts (0.557 moles) of the hindered amine H2, 300 parts of ethyl acetate and 0.3 part of a catalyst (di-n-butyltindilaurate) are introduced into a reaction flask and the temperature is allowed to rise to 35° C. The reaction contents are then heated at 60-65° C. for two hours at which time the NCO value is reduced to <0.8%, whereupon the equivalent amount of ethanol is added, calculated relative to residual NCO, and reaction is continued until the NCO value drops to 0. The solvent is stripped off and the desired product is discharged. The desired product is received as a light orange viscous oil (245 grams) with a glass transition temperature of −2.1° C. Gel permeation chromatography determines the number average molecular weight is 1318 grams/mole and the weight average molecular weight is 2025 grams/mole. The hindered amine light stabilizer is covalently bound to the oligomer.

EXAMPLE S3

Curable Oligomer Containing UV Light Absorber Groups

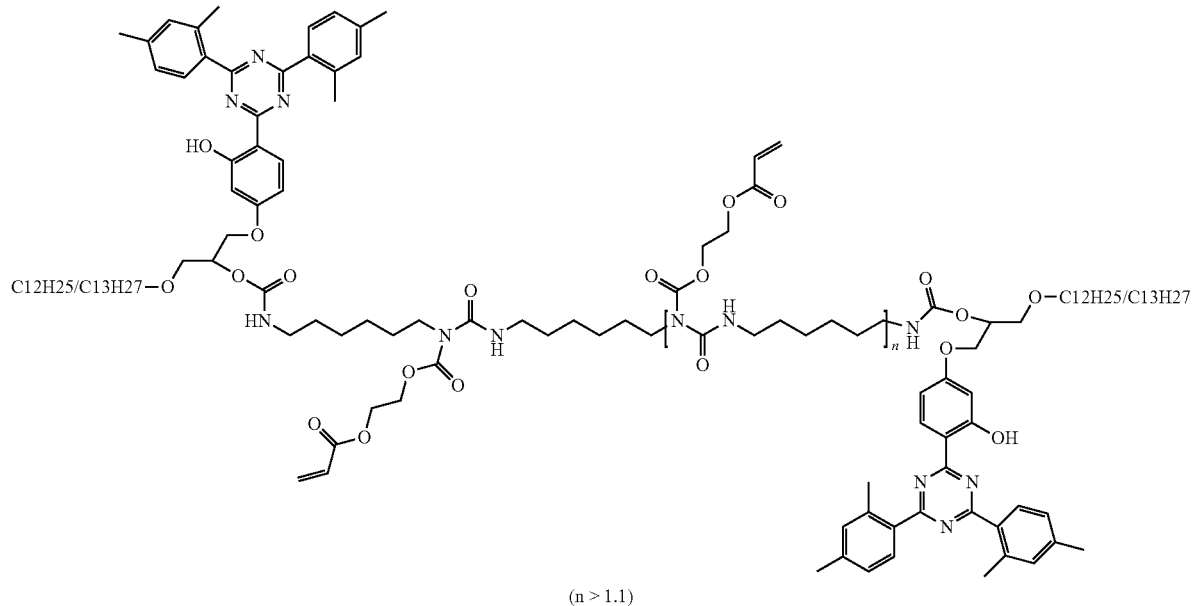

(n > 1.1)

58.7 parts (approximately 0.105 moles, approximately 0.210 moles of NCO groups) of the intermediate allophanate, 132.1 parts (0.205 moles) of the UV6 mixture, 100 parts of ethyl acetate and 0.24 part of a catalyst (di-n-butyltindilaurate) are introduced into a reaction flask and the temperature is allowed to rise to 40-45° C. The reaction contents are then heated at 50-55° C. for four hours at which time the NCO value is reduced to <0.8%, whereupon the equivalent amount of ethanol is added, calculated relative to residual NCO, and reaction is continued until the NCO value drops to 0. The solvent is stripped off and the desired product is discharged. The desired product is received as a light yellow viscous oil (180 grams) and the glass transition temperature is −8.9° C. Gel permeation chromatography determines the number average molecular weight is 1600 grams/mole and the weight average molecular weight is 3900 grams/mole. The UV absorber is covalently bound to the oligomer.

EXAMPLE S4

Curable Oligomer Containing UV Light Absorber Groups

Example S3 is repeated employing 404.2 parts (approximately 0.714 moles, approximately 1.428 moles of NCO groups) of the intermediate allophanate, 782.9 parts (1.21 moles) of the UV absorber mixture, 200 parts of ethyl acetate, 6.0 parts of IRGASTAB UV22 stabilizer and 1.0 part of a catalyst (di-n-butyltindilaurate). The reactants are introduced into a reaction flask and the temperature is allowed to rise to 60-65° C. The reaction contents are then heated at 80-85° C. for one hour at which time the NCO value is reduced to <0.8%, whereupon the equivalent amount of n-butanol is added, calculated relative to residual NCO, and the reaction is continued until the NCO value drops to 0. The solvent is stripped off and the desired product is discharged. The desired product is received as a light yellow viscous oil (1120 grams). Gel permeation chromatography determines the number average molecular weight is 1760 grams/mole and the weight average molecular weight is 2445 grams/mole. The UV absorber mixture is covalently bound to the oligomer.

EXAMPLE S5

Curable Oligomer Containing Hindered Amine Light Stabilizer Groups

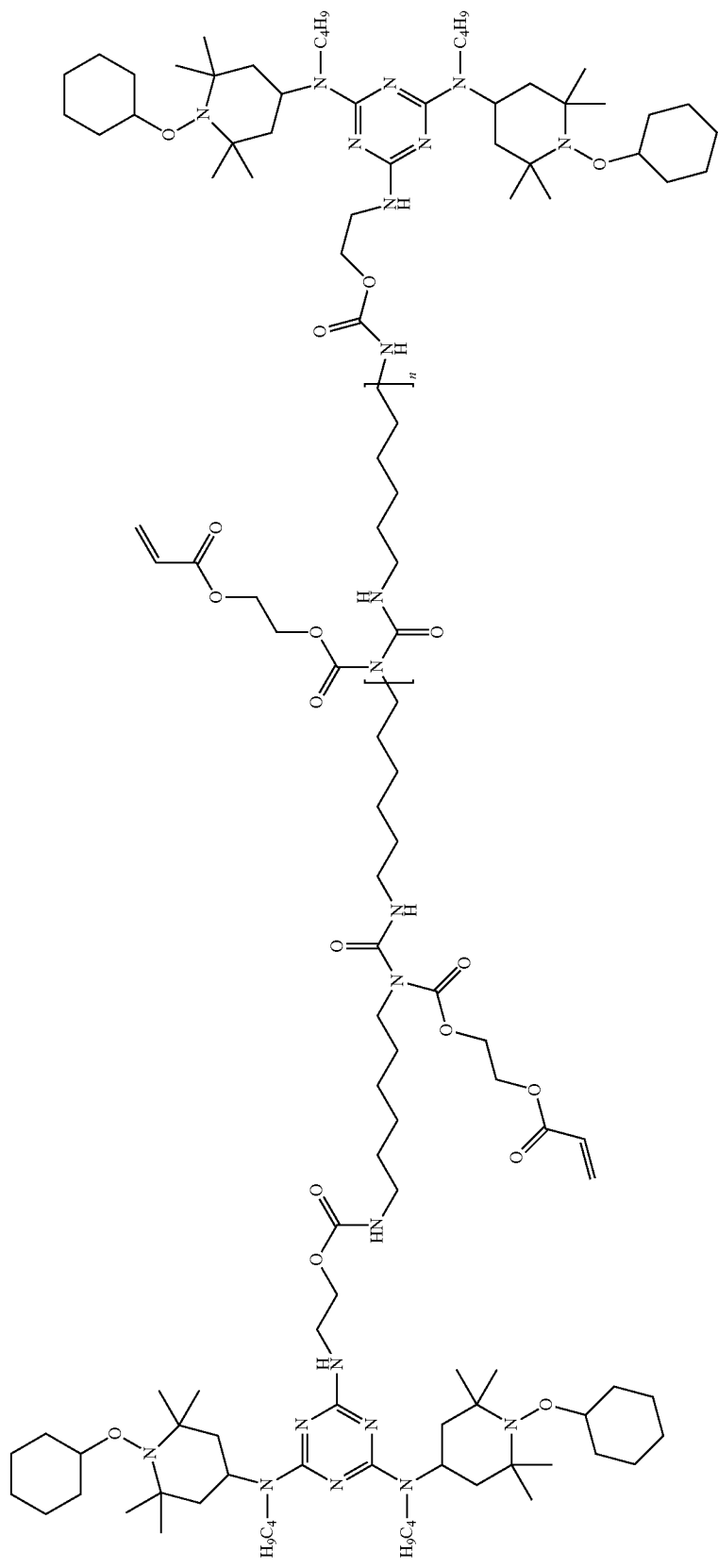

347.5 parts (approximately 0.62 moles, approximately 1.24 moles of NCO groups) of the intermediate allophanate, 936.1 parts (1.24 moles) of the hindered amine H9, 200 parts of ethyl acetate, 6.0 parts of IRGASTAB UV22 stabilizer, and 0.92 part of a catalyst (di-n-butyltindilaurate) are introduced into a reaction flask and the temperature is allowed to rise to 50-55° C. The reaction contents are then heated at 70-75° C. for one hour at which time the NCO value is reduced to <0.8%, whereupon the equivalent amount of n-butanol is added, calculated relative to residual NCO, and reaction is continued until the NCO value drops to 0. The solvent is stripped off and the desired product is discharged. The desired product is received as a light yellow viscous oil (1202 grams). The hindered amine light stabilizer is covalently bound to the oligomer.

EXAMPLE S6

Curable Oligomer Containing Hindered Amine Light Stabilizer Groups

Example S5 is repeated, employing 107 parts (approximately 0.191 moles, approximately 0.382 moles of NCO groups) of the intermediate allophanate, 288.2 parts (0.381 moles) of hindered amine H9, 300 parts of ethyl acetate and 0.4 parts of a catalyst (di-n-butyltindilaurate). The reactants are introduced into a reaction flask and the temperature is allowed to rise to about 35° C. The reaction contents are then heated at 60-65° C. for one hour at which time the NCO value is reduced to <0.8%, whereupon the equivalent amount of ethanol is added, calculated relative to residual NCO, and reaction is continued until the NCO value drops to 0. The solvent is removed by distillation and the desired product is received. The desired product is received as a light yellow viscous oil (342 grams). The hindered amine light stabilizer is covalently bound to the oligomer.

EXAMPLE S7

Curable Oligomers Containing Polymer Stabilizer Groups

Examples S2-S6 are repeated, replacing the hindered amine or UVA with AO1, AO2, AO3, AO4 (ascorbic acid), H3, H6, H10, H11, dibenzylhydroxylamine, diethylhydroxylamine and dihexylhydroxylamine.

The structure of employing AO2 is:

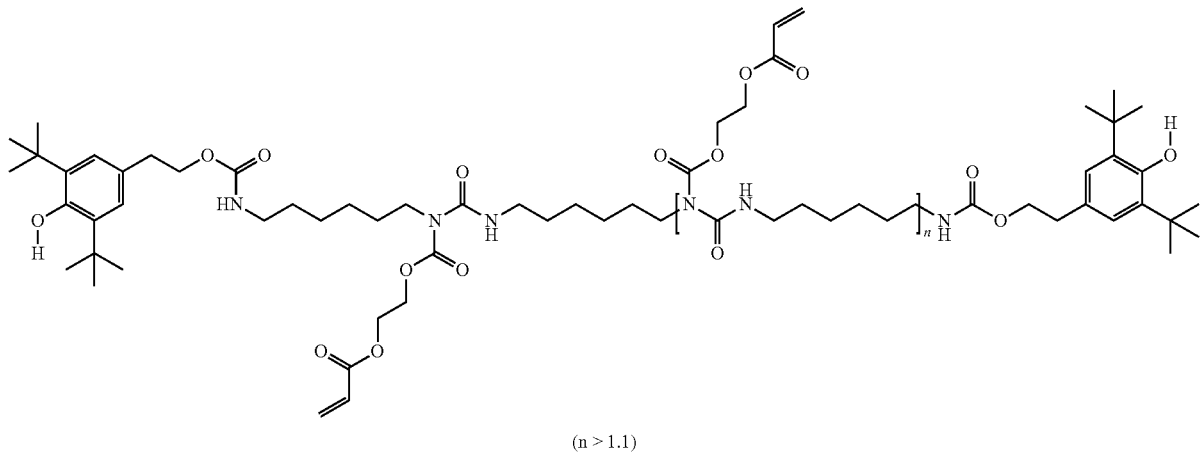

(n > 1.1)

The hindered phenolic hydroxy group is not isocyanate reactive.

The structure of employing diethylhydroxylamine is:

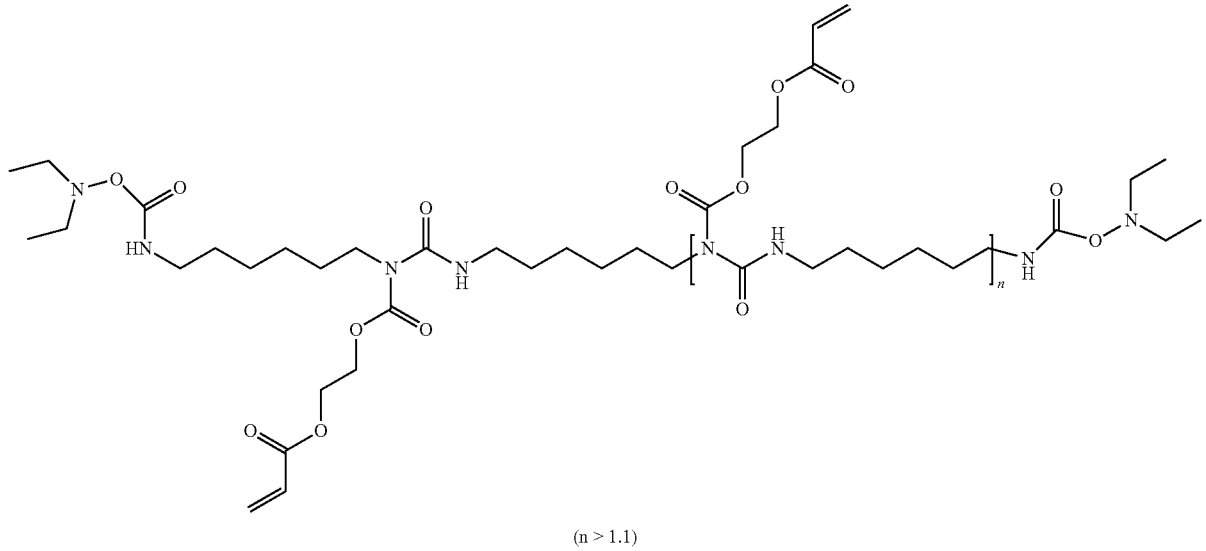

(n > 1.1)

EXAMPLE A1

Solubility

The instant products are added to solvents and/or a monomer and shaken on a LAU shaker at ambient temperature. The solubility is measured and shown below.

| Solvent | Example S4 | Example S6 |
|---|---|---|
| 1 | >90% | >73% |
| 2 | 92% | 68% |
| 3 | 80% | ca. 50% | solvent 1: ethyl acetate
solvent 2: propylene glycol monomethylether acetate
solvent 3: triacrylate of trimethylolpropane ethoxylate (average of 3.5 ethoxylation)

At the concentrations above, all samples are transparent. This indicates that the instant oligomers are soluble and compatible which is highly desirable. The instant compounds can be easily polymerized into a polymer.

EXAMPLE A2

Coating Cure

A solution of 62.77 parts of an aliphatic urethane acrylate (LAROMER LR 8987), 6.30 parts of instant Example S4 (73.0 weight percent solids in ethyl acetate) and 5.28 parts of instant Example S6 (92.3 weight percent solids in ethyl acetate) is prepared. To 17.46 parts of the solution 0.83 parts of a photoinitiator (IRGACURE 2022, 4.54% by weight) are added. This solution is coated using a bird bar onto a Leneta card with a wet film thickness of 2 microns and photocured using a Heraeus Noblelight Fusion UV systems Model DRS—10/12 QN, which is equipped with V & D lamps with adjustable power and conveyor settings. Results are below. Hardness is pendulum swings after 2 passes. UV intensity is $J/cm^2$ for 1 pass.

| % power V + D bulbs | UV intensity | hardness |
|---|---|---|
| 100 | 1.681 | 74 |
| 50 | 0.473 | 62 |
| 30 | 0.154 | 27* |

Conveyor speed is 46 ft/minute.
*Hardness after only one pass.

EXAMPLE A3

Acrylate Bond Conversion

A solution of 82.96 parts of an aliphatic urethane acrylate (LAROMER LR 8987), 7.50 parts of oligomer S4 (73.0 weight percent solids in ethyl acetate), 5.00 parts of oligomer S6 (92.3 weight percent solids in ethyl acetate), and 4.54 parts of a photoinitiator (IRGACURE 2022, 4.54% by weight) is prepared. This solution is coated using a bird bar onto a Leneta card with a wet film thickness of 2 microns and photocured using a Heraeus Noblelight Fusion UV systems Model DRS—10/12 QN, which is equipped with V & D lamps with adjustable power and conveyor settings. The percentage of double bond conversion is measured by FT-IR. Conveyor speed is 46 ft/minute. UV intensity is $J/cm^2$.

| UV intensity | percent acrylate conversion |
|---|---|
| 0 | 0 |
| 0.154 | 58.4 |
| 0.473 | 76.2 |
| 0.946 | 72.9 |
| 1.41 | 81.3 |
| 2.82 | 83.7 |

EXAMPLE A4

Percent UVA Retained after Extraction

A solution of 82.96 parts of an aliphatic urethane acrylate (LAROMER LR 8987), 7.50 parts of instant Example S4 (73.0 weight percent solids in ethyl acetate), 5.00 parts of instant Example S6 (92.3 weight percent solids in ethyl acetate), and 4.54 parts of a photoinitiator (IRGACURE 2022, 4.54% by weight) is prepared. This solution is coated using a bird bar onto a Leneta card with a wet film thickness of 2 microns and photocured using a Heraeus Noblelight Fusion UV systems Model DRS—10/12 QN, which is equipped with V & D lamps with adjustable power and conveyor settings. The films prepared from the formulation above are soaked in tetrahydrofuran (THF) for 24 hours. The percent UV absorber retained is determined by measuring the UV absorbance of the film before and after THF extraction. Results are below. UV intensity is $J/cm^2$. Conveyor speed is 46 ft/minute.

| UV intensity | percent UV absorber retained |
|---|---|
| 0 | 0 |
| 0.154 | 72.0 |
| 0.473 | 84.1 |
| 0.946 | 87.8 |
| 2.82 | 95.5 |

Very little of the UV absorber is removed by extraction when it is covalently bound to the resulting polymer backbone. Conversely, when UV6 itself is substituted for oligomer S4 in the formulation and the formulation is photocured in a similar fashion, over 90% of the UV absorber is removed by extraction. When the molecule is not covalently bound to the substrate, it can migrate out of the substrate and into the environment. The unbound molecule could migrate into a food stuff from a food package or food package label.

EXAMPLE A5

Acrylate Bond Conversion

The formulations below are prepared and determinations are made of the percent acrylate conversion (reaction into polymer) at various power settings.

| component | formulation 1 | formulation 2 |
|---|---|---|
| LAROMER 8987 | 82.96 parts | 82.96 parts |
| IRGACURE 2022 | 4.54 parts | 4.54 parts |
| oligomer S6 | 5.00 parts | 5.00 parts |
| UV6 | — | 7.50 parts |
| oligomer S4 | 7.50 parts | — |

The solutions are coated using a bird bar onto a Leneta card with a wet film thickness of 2 microns and photocured using a Heraeus Noblelight Fusion UV systems Model DRS—10/12 QN, which is equipped with V & D lamps with adjustable power and conveyor settings. The wet film thickness for all films is 2 microns. The percentage of double bond (acrylate) conversion is measured by FT-IR and shown below. Conveyor speed is 46 ft/minute. UV intensity is J/cm$^2$.

| UV intensity | formulation 1 | formulation 2 |
|---|---|---|
| 0 | 0 | 0 |
| 0.11 | 53 | 21 |
| 0.49 | 81 | 49 |
| 1.52 | 86 | 67 |

This example demonstrates that the UV absorber without the acrylate functionality actually hinders photocuring of the formulation which presents a significant disadvantage.

The invention claimed is:

1. An oligomer containing one or more ethylenically unsaturated groups bound through allophanate groups and/or carbamate groups and containing at least one polymer stabilizer group covalently bound through allophanate groups and/or carbamate groups, wherein the oligomer is derived from a) one or more organic polyisocyanates, b) one or more compounds containing at least one isocyanate reactive group and at least one ethylenically unsaturated group and c) one or more compounds, containing at least one isocyanate reactive group and the at least one polymer stabilizer group, selected from the group consisting of H1-H11, UV1-UV7, AO1-AO3,

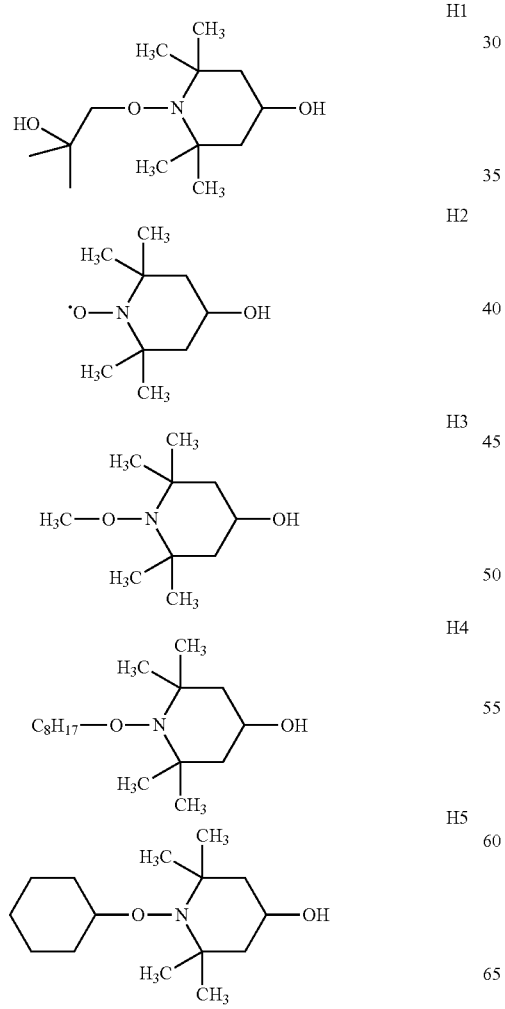
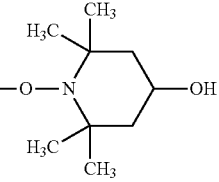
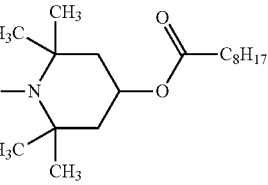
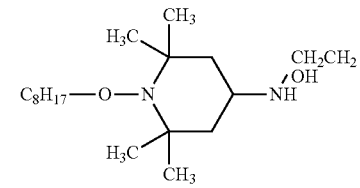
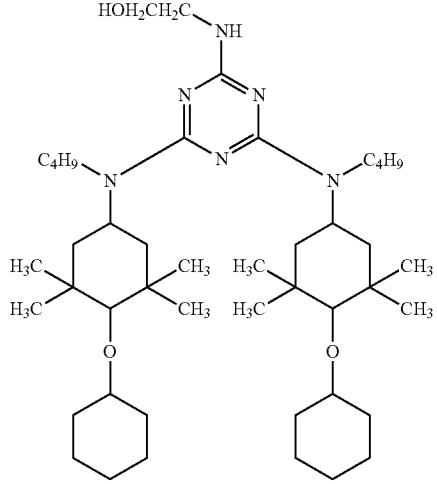
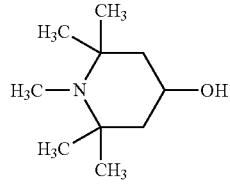
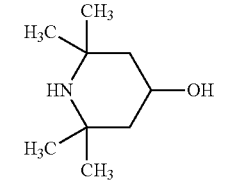
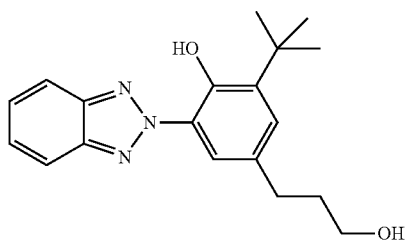

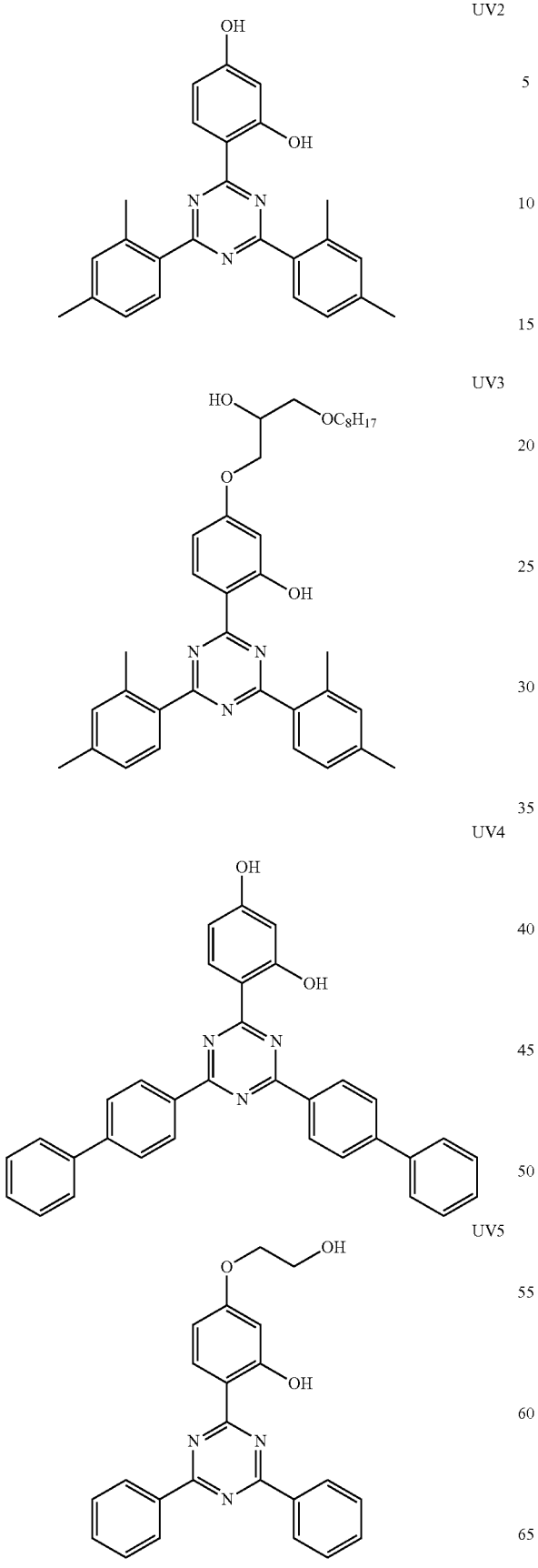
N,N-dibenzylhydroxylamine, N,N-diethylhydroxylamine, N,N-dihexylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N- dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine and N-methyl-N-octadecylhydroxylamine and N,N-di(C$_{16}$-C$_{18}$alkyl)hydroxylamine.

2. An oligomer according to claim 1 derived from

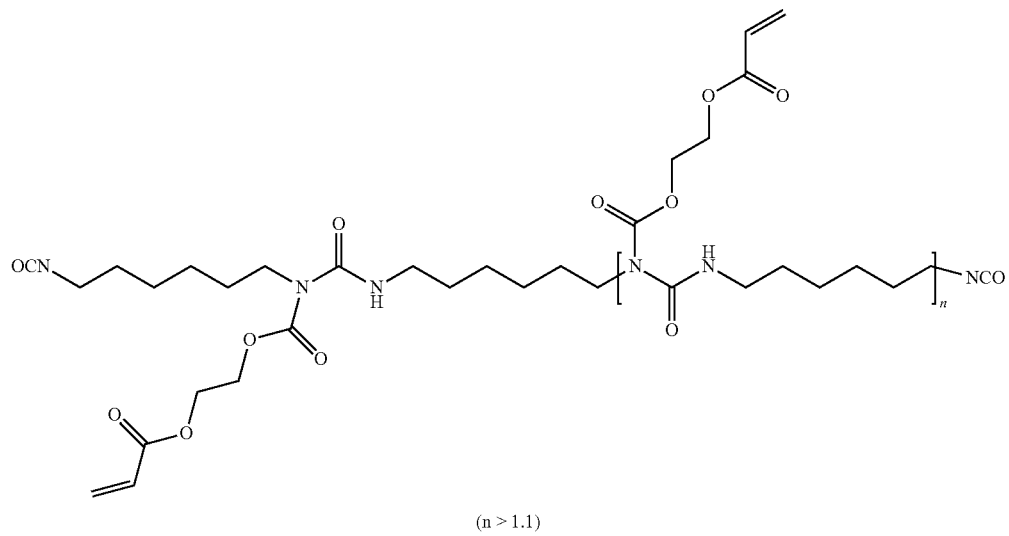

(n > 1.1)

and one or more compounds, containing at least one isocyanate reactive group and at least one polymer stabilizer group, selected from the group consisting of H1-H11, UV1-UV7, AO1-AO3,

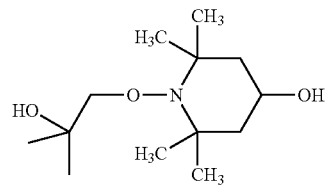
H1

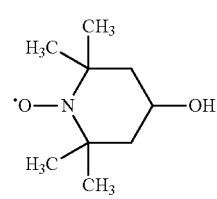
H2

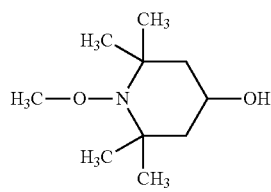
H3

-continued

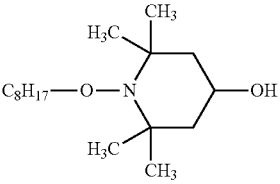
H4

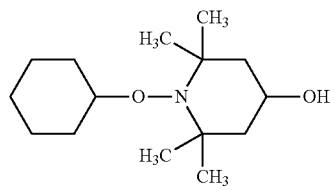
H5

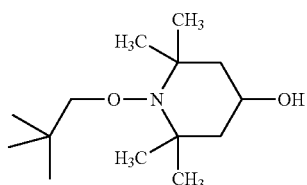
H6

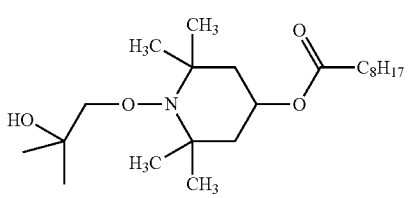
H7

| | |
|---|---|
| H8 | 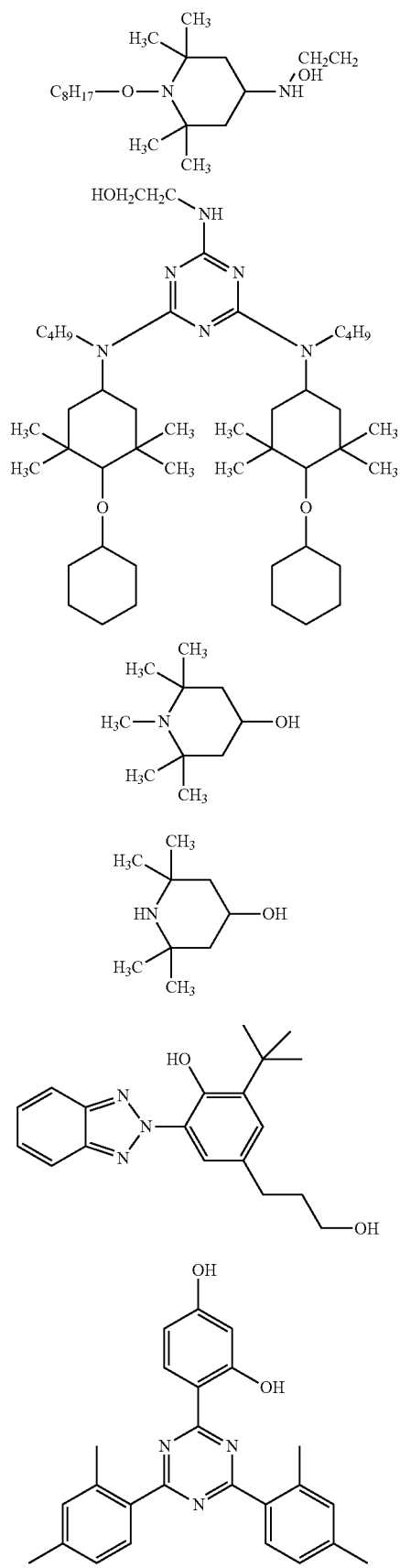 |
| H9 | |
| H10 | |
| H11 | |
| UV1 | |
| UV2 | |
| | |
|---|---|
| UV3 | 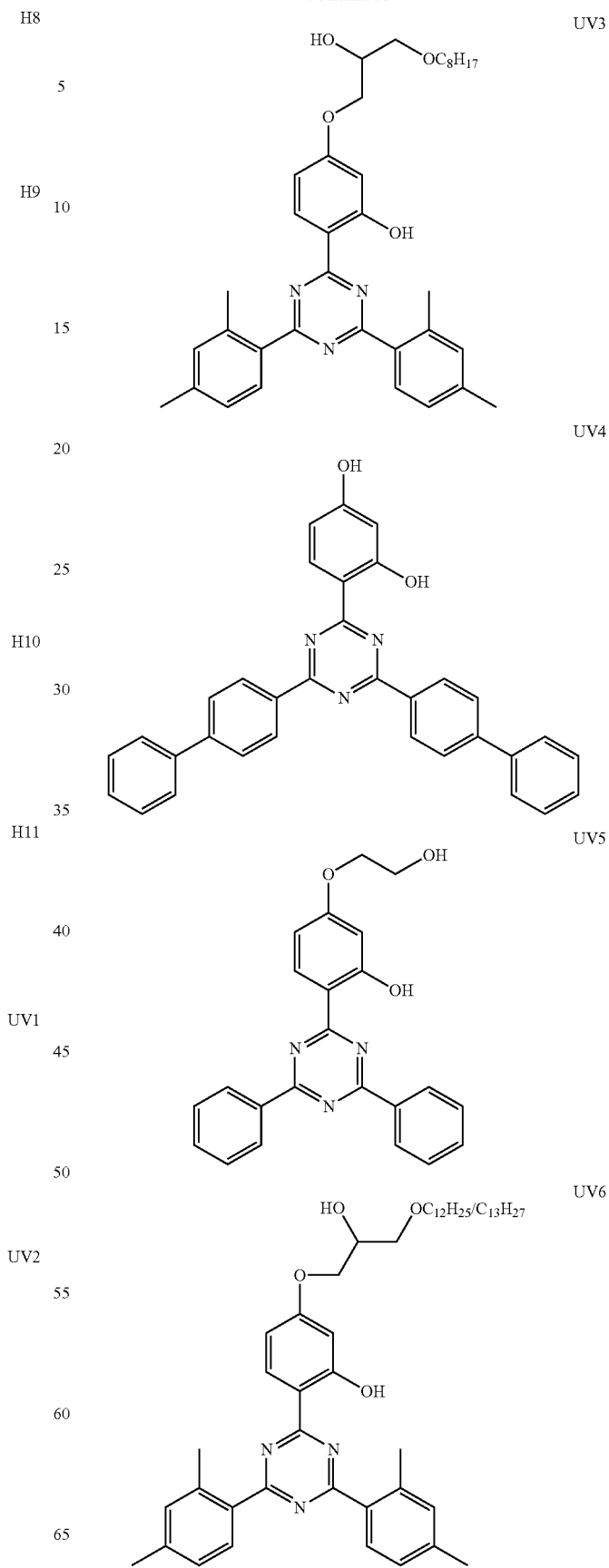 |
| UV4 | |
| UV5 | |
| UV6 | |

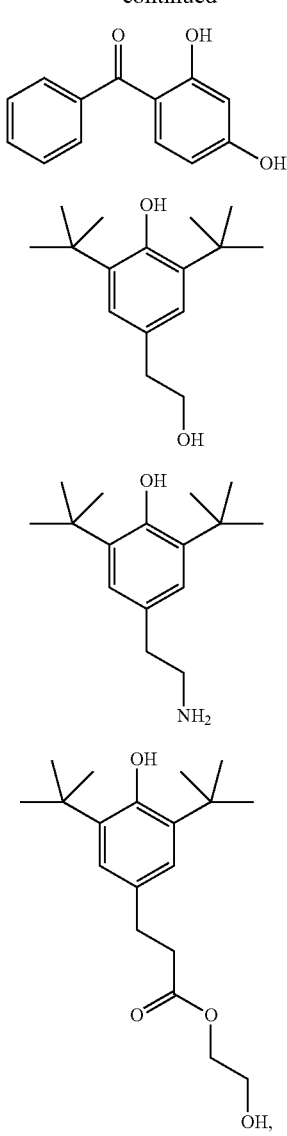
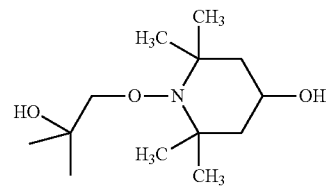
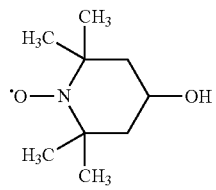
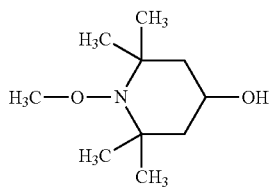
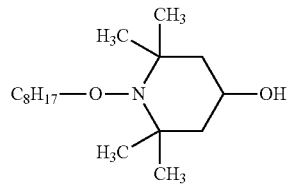
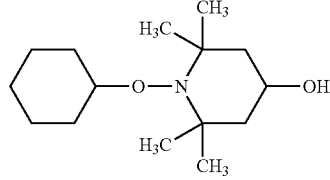
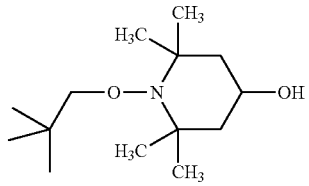

N,N-dibenzylhydroxylamine, N,N-diethylhydroxylamine, N,N-dihexylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine and N,N-di($C_{16}$-$C_{18}$alkyl) hydroxylamine.

3. An oligomer according to claim 1 where the number average molecular weight is from about 900 to about 3000 g/mol.

4. A curable coating, ink or varnish composition comprising an oligomer according to claim 1.

5. A curable composition according to claim 4 further comprising a photoinitiator.

6. A process for the preparation of an oligomer according to claim 1, which process comprises reacting a) one or more organic polyisocyanates, b) one or more compounds containing at least one isocyanate reactive group and at least one ethylenically unsaturated group and c) one or more compounds, containing at least one isocyanate reactive group and at least one polymer stabilizer group, selected from the group consisting of H1-H11, UV1-UV7, AO1-AO3, -continued
H8 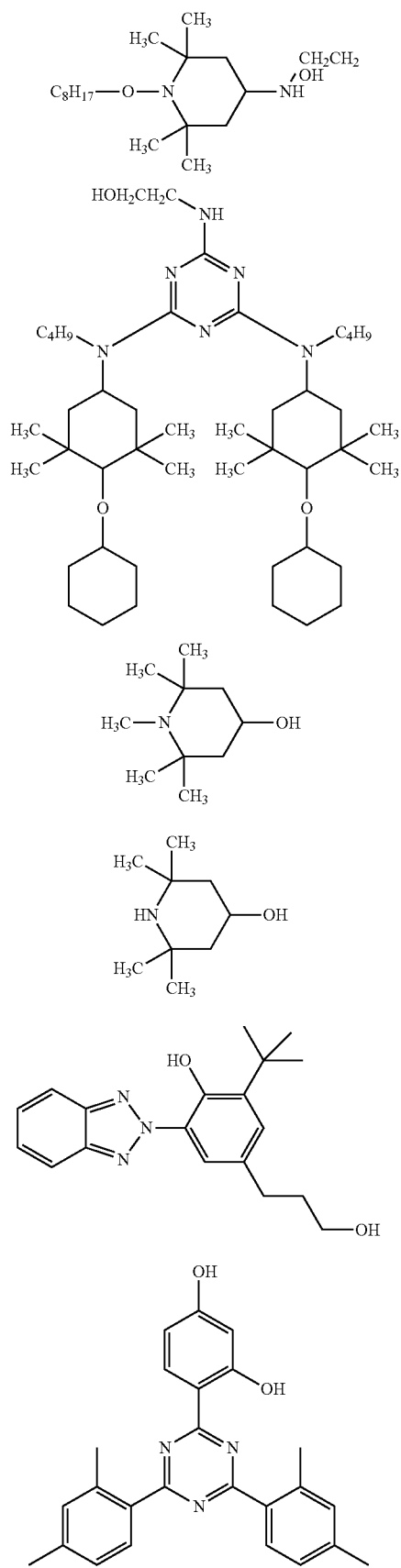
H9
H10
H11
UV1
UV2
-continued
UV3 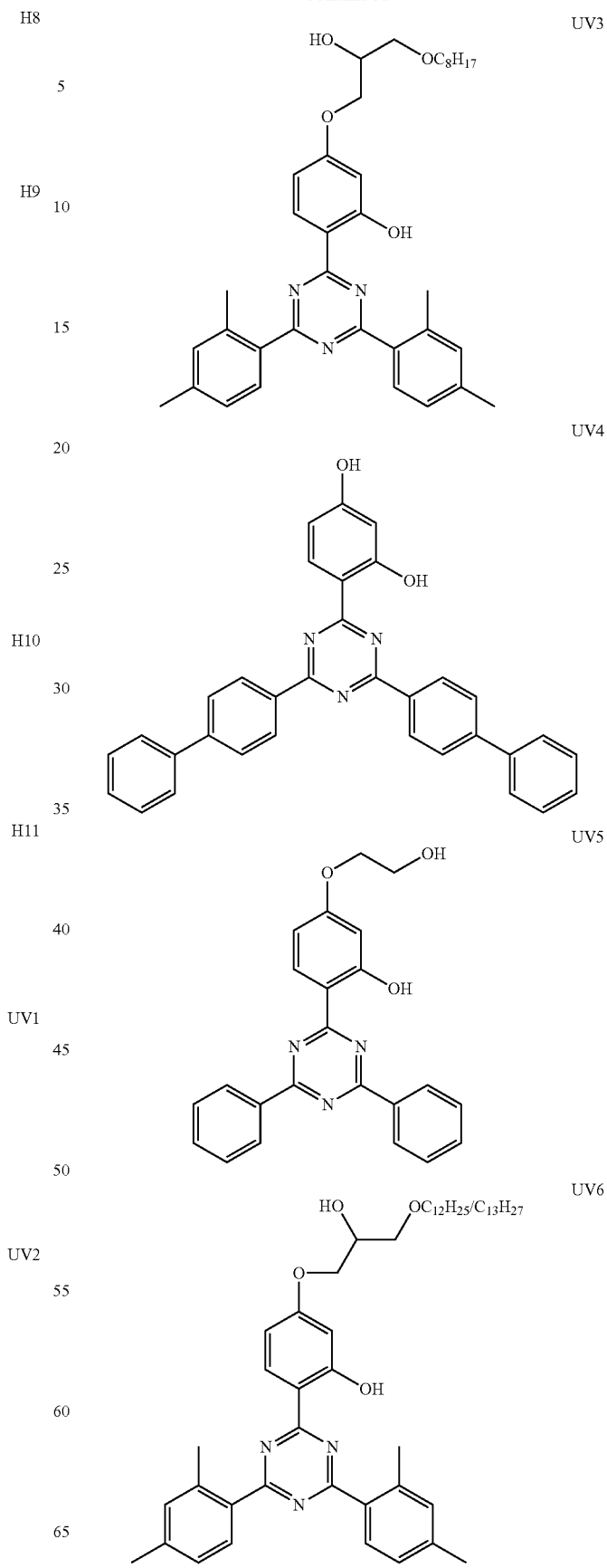
UV4
UV5
UV6

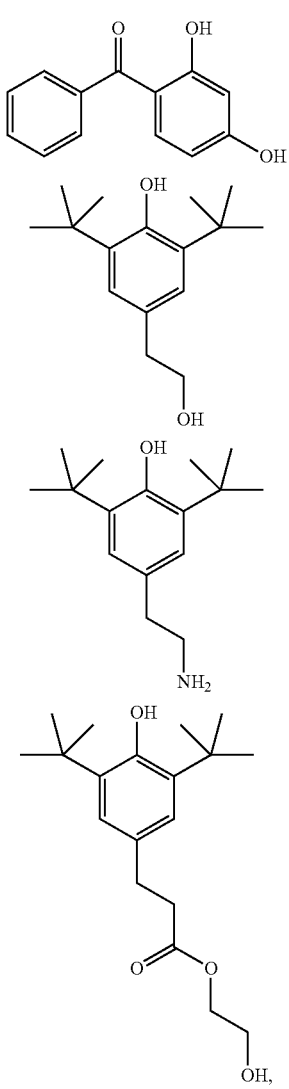

UV7

AO1

AO2

AO3

N,N-dibenzylhydroxylamine, N,N-diethylhydroxylamine, N,N-dihexylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine and N,N-di($C_{16}$-$C_{18}$alkyl) hydroxylamine, neat or in the presence of a suitable solvent, in the presence of a suitable catalyst and at a suitable temperature.

7. A process according to claim 6 where a) and b) are reacted to form an intermediate with allophanate bound ethylenically unsaturated groups and unreacted isocyanate groups, followed by reacting the intermediate with c) or a) and c) are reacted to form an intermediate with allophanate bound polymer stabilizer groups and unreacted isocyanate groups, followed by reacting the intermediate with b) or a), b) and c) are reacted in a 1 step process.

8. An oligomer according to claim 1 where the number average molecular weight is from about 1000 to about 2500 g/mol.

9. An oligomer according to claim 1 where the number average molecular weight is from about 1000 to about 2000 g/mol.

* * * * *